US006288293B1

(12) United States Patent
Wanzke et al.

(10) Patent No.: US 6,288,293 B1
(45) Date of Patent: Sep. 11, 2001

(54) PROCESS FOR THE PREPARATION OF 1,1,1, 2-TETRAFLUOROETHANE

(75) Inventors: Wolfgang Wanzke, Frankfurt am Main; Günter Siegemund; Wilfried Schmieder, both of Hofheim am Taunus, all of (DE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 08/080,449

(22) Filed: Jun. 21, 1993

Related U.S. Application Data

(63) Continuation of application No. 07/954,412, filed on Sep. 30, 1992, now abandoned, which is a continuation of application No. 07/580,588, filed on Sep. 11, 1990, now abandoned.

(30) Foreign Application Priority Data

Sep. 13, 1989 (DE) .................................. 39 30 507

(51) Int. Cl.⁷ ..................................... C07C 17/08
(52) U.S. Cl. ........................ 570/168; 570/166; 570/169
(58) Field of Search .................... 570/168, 169, 570/166

(56) References Cited

U.S. PATENT DOCUMENTS 3,992,325  11/1976  Knaak .
4,129,603  12/1978  Bell .
4,158,675   6/1979  Potter .
4,547,483  10/1985  Müller et al. .

FOREIGN PATENT DOCUMENTS 2806865  10/1978  (DE) .
2932934   6/1988  (DE) .
0317981   5/1989  (EP) .

OTHER PUBLICATIONS

Patent Abstracts of Japan, vol. 7, No. 46 (C–153) (1191), Feb. 23, 1983 (JP–A–57197232, published Dec. 3, 1982).
Patent Abstracts of Japan, vol. 4, No. 54 (C–8) (536), Apr. 23, 1980 (JP–A–5527139, published Feb. 27, 1980).
Marangoni, L. et al, *Chim. Ind.* 64:135–140 (1982).

*Primary Examiner*—Alan Siegel
(74) *Attorney, Agent, or Firm*—Connolly Bove Lodge & Hutz LLP

(57) ABSTRACT

The invention relates to a process for the preparation of 1,1,1,2-tetrafluoroethane from 1,1,1-trifluoro-2-chloroethane and hydrogen fluoride in the gas phase, in which a catalyst containing chromium and magnesium is used which is obtainable by precipitating chromium(III) hydroxide by reacting 1 mol of a water-soluble chromium (III) salt with at least 1.5 mol of magnesium hydroxide or magnesium oxide in the presence of water, the reaction mixture is made into a paste containing chromium hydroxide and a magnesium salt, and the paste is then dried and treated with hydrogen fluoride at temperatures of 20 to 500° C.

10 Claims, No Drawings

PROCESS FOR THE PREPARATION OF 1,1,1,2-TETRAFLUOROETHANE

This application is a continuation of application Ser. No. 07/954,412 filed on Sep. 30, 1992 now abandoned, which is a continuation of application Ser No. 07/580,588 filed on Sep. 11, 1990 now abandoned.

The invention relates to a process for the preparation of 1,1,1,2-tetrafluoroethane by reaction of 1,1,1-trifluoro-2-chloroethane with hydrogen fluoride in the gas phase.

1,1,1,2-Tetrafluoroethane (which hereinafter is also called tetrafluoroethane) can be used as a chlorine-free substitute for difluorodichloromethane (R 12) in refrigeration and air-conditioning technology.

It is already known that tetrafluoroethane can be obtained in the reaction of 1,1,1-trifluoro-2-chloroethane (hereinafter also called trifluorochloroethane) with hydrogen fluoride over suitable catalysts not only in the gas phase but also in the liquid phase. The catalysts which have been described for the gas phase reaction are predominantly solids either composed completely of chromium(III) compounds or containing a chromium(III) salt on a support material such as alumina. German Offenlegungsschrift 2,806,865 (=U.S. Pat. No. 4,129,603) describes the use of a chromium oxide catalyst which is preferably obtained by treatment of a chromium hydroxide paste with steam and is then converted with hydrogen fluoride into a chromium oxyfluoride. German Patent 2,932,934 describes the use of various chromium (III) compounds as catalysts, for example chromium(III) fluoride or other salts, which are converted by a hydrogen fluoride treatment into chromium oxyfluoride or chromium (III) fluoride.

The processes mentioned still have various drawbacks, which are unfavorable especially for industrial preparation of tetrafluoroethane. The reason is that in addition to tetrafluoroethane other compounds, including 1,1-difluoro-2-chloroethene, which is difficult to separate off from the desired product by distillation, are additionally formed.

According to the process of German Offenlegungsschrift 2,806,865, either a second reactor is required to react the 1,1-difluoro-2-chloroethene contained in the crude product again at lower temperatures, or it has to be separated off by a wet chemical method, using permanganate solution, which in both cases requires a substantial additional expenditure. The selectivities obtained with the chromium oxyfluoride catalyst before separating off 1,1-difluoro-2-chloroethene are 91–95%.

The catalysts described in German Patent 2,932,934 achieve on a short-term basis a higher selectivity for tetrafluoroethane (up to 98%) at temperatures around 400° C., although the residual content of 1,1-difluoro-2-chloroethene is not indicated. However, the chromium(III) catalysts used lose a substantial amount of their activity after as little as 44 hours, which can be compensated by continuously metering in a certain amount of oxygen. However, the additional metering of oxygen into the reactor, apart from the increased technical expenditure, leads to further problems during the work-up of the product. Oxygen makes the compression or condensation of the product more difficult and has a very detrimental effect in dissolved form on the application of tetrafluoroethane in refrigeration and air-conditioning technology. In addition, if too much oxygen is metered into the reactor, the selectivity for tetrafluoroethane again diminishes.

The catalyst described by Marangoni et al. (Chim. Ind. 64, 135 (1982)) and composed of precipitated chromium hydroxide reaches a tetrafluoroethane selectivity of only 79% at 350° C. over a period of 60 hours.

It has now been found that the catalyst described in European Patent 130,532 (=U.S. Pat. No. 4,547,483) and composed of magnesium fluoride and a fluorine-containing chromium(III) compound allows the conversion of trifluorochloroethane into tetrafluoroethane with a surprisingly high selectivity and long-lasting activity. This catalyst is used in the not yet published German Patent Application P 3,923,256.5 for the preparation of the starting material 1,1,1-trifluoro-2-chloroethane.

The invention relates to a process for the preparation of 1,1,1,2-tetrafluoroethane from 1,1,1-trifluoro-2-chloroethane and hydrogen fluoride in the gas phase, which process comprises using a catalyst containing chromium and magnesium which is obtainable by precipitating chromium (III) hydroxide by reacting 1 mol of a water-soluble chromium(III) salt with at least 1.5 mol of magnesium hydroxide or magnesium oxide in the presence of water, making the reaction mixture into a paste containing chromium hydroxide and a magnesium salt, and then drying the paste and treating it at temperatures of 20 to 500° C. with hydrogen fluoride.

The catalyst for the gas phase reaction according to the invention is particularly effective under superatmospheric pressure, since it substantially reduces the content of olefinic by-products in the product mixture, in particular that of 1,1-difluoro-2-chloroethene. In this manner, the olefin content in the crude product can be reduced to values below 100 ppm without using a second reactor at lower temperature or a chemical wash, such as described in German Offenlegungsschrift 2,806,865. During the reaction, the pressure in the reactor is set to 1–26 bar, preferably 5–15 bar, by means of a control valve.

In the gas phase reaction according to the invention, the catalyst shows no loss in activity over a longer period of time compared with the catalyst described in German Patent 2,932,934, so that it does not need the additional metering in of oxygen and thus the technical disadvantages mentioned are avoided.

The process according to the invention can be carried out, for example, in such a manner that the starting materials trifluorochloroethane and hydrogen fluoride are fed continuously into an evaporator made of stainless steel or nickel. The temperature of the evaporator is not critical but has to be sufficient for transferring both components completely into the gas phase at the pressure chosen. The gaseous starting materials are passed, if desired via a preheating section and a gas mixer, into the reactor which contains a bed composed of the catalyst described in EP-OS 130,532. The reactor is also made of stainless steel or nickel and can be used in various technical designs, for example as shaft, tubular or annular gap reactor.

The temperature of the catalyst bed is maintained at 250–450° C., preferably at 320–380° C., by heating the reactor.

To obtain the highest possible conversion of trifluorochloroethane and a very high selectivity for tetrafluoroethane at the reaction temperatures given, hydrogen fluoride is preferably used in excess. The molar ratio of hydrogen fluoride/trifluorochloroethane is in general at least 1:1; the upper limit of the molar ratio is only determined by economic considerations. Preferably, it is 2:1 to 10:1, in particular 4:1 to 8:1.

Unconverted trifluorochloroethane can be recycled into the reactor.

The process according to the invention will be illustrated in more detail by the examples which follow.

Test Report

A (Preparation of the Catalyst According to European Patent 130,532)

200 g of $Cr(NO_3)_3 \times 9\, H_2O$ were dissolved in 1 l of water. This solution was added to a mixture of 500 g of magnesium oxide and 240 g of graphite, and the resulting paste-like material was thoroughly kneaded.

The paste-like reaction product was then granulated to give cubes (edge length 0.5 cm) and dried at 100° C. for 16 hours.

1 l (bulk volume) of the dried catalyst bodies (=600 g) was treated in a nickel or stainless steel tube of 5 cm clear width and 100 cm length at 200° C. with 15 mol of hydrogen fluoride. The duration of the hydrogen fluoride treatment was about 6 hours. During this process, the hydrogen fluoride was diluted with $N_2$. The fluorination catalyst obtained had a chromium content of 2.3% by weight.

B (Preparation of the Catalyst According to European Patent 130,532)

200 g of $Cr(NO_3)_3 \times 9\, H_2O$ were dissolved in 278 ml of water. This solution was added to a mixture of 138 g of magnesium oxide and 136 g of graphite. The further processing and hydrogen fluoride treatment was carried out analogously to test report A. The ready-to-use fluorination catalyst contained 4.3% by weight of chromium.

EXAMPLE 1

120 g of trifluorochloroethane and 120 g of hydrogen fluoride (molar ratio 1:5.9) per hour were passed as a gas over 1 l of the catalyst prepared according to test report A in a tubular reactor which was maintained at a temperature of 360° C. by means of an electric heating coil.

The tubular reactor was the same as that which had already been used for the hydrogen fluoride treatment during the preparation of the catalyst.

The gaseous reaction products leaving the reactor were fed into a wash tank filled with water or potassium hydroxide solution, in which the hydrogen chloride formed and the excess hydrogen fluoride were collected.

The gaseous water-insoluble reaction products were analyzed by gas chromatography.

After 6 hours at atmospheric pressure, the conversion was 27.4%, relative to the trifluorochloroethane used. The selectivity for tetrafluoroethane was 96.4%, relative to the trifluorochloroethane converted.

The reaction product contained 26.4% by weight of $CF_3$—$CH_2F$, 0.23% by weight of $CF_2$=$CHCl$ and 0.77% by weight of other components in addition to unconverted $CF_3$—$CH_2Cl$.

EXAMPLE 2

The catalyst prepared according to test report A was used for the reaction of trifluorochloroethane with hydrogen fluoride in the same experimental setup as in Example 1. 120 g of trifluorochloroethane per hour and 120 g of hydrogen fluoride per hour were passed as a gas over the catalyst at 360° C. and a pressure of 10 bar.

After 20 hours, the conversion was 26.6%, relative to the trifluorochloroethane used. The selectivity for tetrafluoroethane was 97.5%, relative to the converted trifluorochloroethane.

The reaction product contained 25.9% by weight of $CF_3$—$CH_2F$, 0.009% by weight of $CF_2$=$CHCl$ and 0.69% by weight of other components in addition to unconverted $CF_3$—$CH_2Cl$.

EXAMPLE 3

The catalyst prepared according to test report A was used for the reaction of trifluorochloroethane with hydrogen fluoride in the same experimental setup as in Example 1. 120 g of trifluorochloroethane per hour and 160 g of hydrogen fluoride (molar ratio 1:7.9) per hour were passed as a gas over the catalyst at 360° C. and a pressure of 10 bar.

After 6 hours, the conversion was 28.3%, relative to the trifluorochloroethane used. The selectivity for tetrafluoroethane was 97.9%, relative to the converted trifluorochloroethane.

The reaction product contained 27.7% by weight of $CF_3$—$CH_2F$, 0.006% by weight of $CF_2$=$CHCl$ and 0.6% by weight of other components in addition to unconverted $CF_3$—$CH_2Cl$.

EXAMPLE 4

The catalyst prepared according to test report A was used for the reaction of trifluorochloroethane with hydrogen fluoride in the same experimental setup as in Example 1. 120 g of trifluorochloroethane per hour and 120 g of hydrogen fluoride per hour were passed as a gas over the catalyst at 360° C. and a pressure of 10 bar. Table 1 shows the conversion of trifluorochloroethane and the selectivity for tetrafluoroethane as a function of the reaction time.

TABLE 1

| Reaction time (h) | Conversion (%) | Selectivity (%) |
|---|---|---|
| 5 | 27.1 | 97.2 |
| 22 | 26.5 | 96.7 |
| 32 | 26.1 | 97.1 |
| 55 | 26.4 | 97.5 |
| 81 | 26.6 | 97.2 |
| 90 | 26.5 | 97.3 |

EXAMPLE 5

The catalyst prepared according to test report B was used for the reaction of trifluorochloroethane with hydrogen fluoride in the same experimental setup as in Example 1. 120 g of trifluorochloroethane per hour and 120 g of hydrogen fluoride per hour were passed as a gas over the catalyst at 360° C.

After 5 hours, the conversion was 29.2%, relative to the trifluorochloroethane used. The selectivity for tetrachloroethane was 95.7%, relative to the converted trifluorochloroethane.

The reaction product contained 27.9% by weight of $CF_3$—$CH_2F$, 0.28% by weight of $CF_2$=$CHCl$ and 1.02% by weight of other components in addition to unconverted $CF_3$—$CH_2Cl$.

EXAMPLE 6

The catalyst prepared according to test report A was used for the reaction of trifluorochloroethane with hydrogen fluoride in the same experimental setup as in Example 1. 120 g of trifluorochloroethane per hour and 120 g of hydrogen fluoride per hour were passed as a gas over the catalyst at 420° C.

After 5 hours, the conversion was 36.3%, relative to the trifluorochloroethane used. The selectivity for tetrafluoroethane was 81.5%, relative to the converted trifluorochloroethane.

The reaction product contained 29.6% by weight of $CF_3$—$CH_2F$, 2.2% by weight of $CF_2$=$CHCl$ and 4.5% by weight of other components in addition to unconverted $CF_3$—$CH_2Cl$.

What is claimed is:

1. A process for the preparation of 1,1,1,2-tetrafluoroethane from 1,1,1,-trifluoro-2-chloroethane and hydrogen fluoride in the gas phase, which process comprises using a catalyst containing chromium and magnesium which is obtained by precipitating chromium(III) hydroxide by reacting 1 mol of a water-soluble chromium(III) salt with at least 1.5 mol of magnesium hydroxide or magnesium oxide in the presence of water, making the reaction mixture into a paste containing chromium hydroxide and a magnesium salt, and then drying the paste and treating it at temperatures of 20 to 500° C. with hydrogen fluoride.

2. The process as claimed in claim 1, wherein the reaction of 1,1,1-trifluoro-2-chloroethane with hydrogen fluoride is carried out in the temperature region of 250–450° C.

3. The process as claimed in claim 1, wherein the reaction of 1,1,1-trifluoro-2-chloroethane with hydrogen fluoride is carried out in the temperature region of 320–380° C.

4. The process as claimed in claim 1, wherein the reaction of 1,1,1-trifluoro-2-chloroethane with hydrogen fluoride is carried out under a pressure of 1–26 bar.

5. The process as claimed in claim 1, wherein the reaction of 1,1,1-trifluoro-2-chloroethane with hydrogen fluoride is carried out under a pressure of 5–15 bar.

6. The process as claimed in claim 1, wherein hydrogen fluoride and 1,1,1-trifluoro-2-chloroethane are used in a molar ratio of 4:1 to 8:1.

7. The process as claimed in claim 1, wherein hydrogen fluoride and 1,1,1-trifluoro-2-chloroethane are used in a molar ratio of at least 1:1.

8. The process as claimed in claim 1, wherein the trifluorochloroethane that is unconverted is recycled into the reactor.

9. The process as claimed in claim 1, wherein a conversion of 26.1 to 29.2%, relative to the trifluorochloroethane used is achieved and a selectivity from 95.7 to 97.9 for the tetrafluoroethane relative to the converted trifluorochloroethane is achieved.

10. The process as claimed in claim 9, wherein the selectivity is from 96.4 to 97.9 and the conversion is from 27.4 to 28.3%.

* * * * *